United States Patent
Utschig et al.

(10) Patent No.: US 7,455,849 B2
(45) Date of Patent: Nov. 25, 2008

(54) AQUEOUS, NON-ALCOHOLIC LIQUID POWDER FORMULATIONS

(75) Inventors: Julie Marie Utschig, Appleton, WI (US); Keisha Lori Clarke, Appleton, WI (US); Wael Rafat Joseph, Appleton, WI (US); David William Koenig, Menasha, WI (US); Duane Gerard Krzysik, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 803 days.

(21) Appl. No.: 10/944,361

(22) Filed: Sep. 16, 2004

(65) Prior Publication Data

US 2006/0057217 A1 Mar. 16, 2006

(51) Int. Cl.
*A61K 8/00* (2006.01)
*A61K 9/14* (2006.01)

(52) U.S. Cl. .................................. 424/401; 424/489
(58) Field of Classification Search .................. 424/401, 424/489
See application file for complete search history.

(56) References Cited

U.S. PATENT DOCUMENTS

| | | | |
|---|---|---|---|
| 5,338,535 | A | 8/1994 | Berndt |
| 5,824,323 | A | 10/1998 | Fishman |
| 5,928,660 | A | 7/1999 | Kobayashi et al. |
| 6,074,672 | A | 6/2000 | Dobkowski et al. |
| 6,221,498 | B1 | 4/2001 | Takahama et al. |
| 6,290,941 | B1 | 9/2001 | Lahanas et al. |
| 6,306,411 | B1 | 10/2001 | Jager Lezer |
| 6,403,704 | B1 | 6/2002 | Bara |
| 6,458,372 | B1 * | 10/2002 | Scordamaglia-Crockett et al. ............ 424/401 |
| 6,660,281 | B1 | 12/2003 | Nakanishi et al. |
| 6,696,049 | B2 | 2/2004 | Vatter et al. |
| 2002/0018790 | A1 | 2/2002 | Vatter et al. |
| 2003/0072780 | A1 | 4/2003 | Ionita-Manzatu et al. |

FOREIGN PATENT DOCUMENTS

| | | |
|---|---|---|
| EP | 1 065 234 B1 | 11/2002 |
| EP | 1 062 944 B1 | 3/2004 |
| JP | 58-039609 A | 3/1983 |
| JP | 05-065212 A | 3/1993 |
| JP | 06-279251 A | 10/1994 |

OTHER PUBLICATIONS

Adamson, Arthur W., "Emulsions and Foams," *Physical Chemistry of Surfaces*, Second Edition, Interscience Publishers, John Wiley & Sons, Inc., 1967, pp. 520-522.

Becher, Paul, "Emulsification," Chapter 18, *Nonionic surfactants*, edited by Martin J. Schick, published by Marcel Dekker, Inc., New York, 1966, pp. 604-626.

Knüttel, A. et al., "New Method For Evaluation of In Vivo Scattering and Refractive Index Properties Obtained With Optical Coherence Tomography," *Journal of Biomedical Optics*, vol. 9, No. 2, Mar./Apr. 2004, pp. 265-273.

Pressman, Norman J., "Markovian Analysis of Cervical Cell Images," *The Journal of Histochemistry & Cytochemistry*, vol. 24, No. 1, The Histochemical Society, Inc., 1976, pp. 138-144.

* cited by examiner

*Primary Examiner*—Johann Richter
*Assistant Examiner*—Konata M. George
(74) *Attorney, Agent, or Firm*—R. Joseph Foster, III; Patricia A. Charlier

(57) ABSTRACT

The present invention is an aqueous, non-alcoholic liquid powder formulation. The aqueous, non-alcoholic liquid powder formulation comprises from about 14% to about 75% by weight of the formulation of water, from about 25% to about 60% by weight of the formulation of a powder, from about 0.05% to about 1% by weight of the formulation of a polymeric emulsifier, from about 0.5% to about 15% by weight of the formulation of a low molecular weight silicone wherein the low molecular weight silicone has an average molecular weight of about 10,000 or less, and from about 0.1% to about 10% by weight of the formulation of a high molecular weight silicone wherein the high molecular weight silicone has an average molecular weight of about 100,000 or greater. The aqueous, non-alcoholic liquid powder formulation may have an optical uniformity index of about 0.1 or less. The aqueous, non-alcoholic liquid powder formulation may have an extensive uniformity index of about 300 or greater.

68 Claims, No Drawings

AQUEOUS, NON-ALCOHOLIC LIQUID POWDER FORMULATIONS

BACKGROUND OF THE INVENTION

Topical formulations for application to the skin take a variety of forms, ranging from dry powders, such as talc and corn starch, to liquids, such as lotions or creams, to solids or semi-solids, such as antiperspirants. Each of these forms provides certain advantages to the users which may determine the selection of the products incorporating the formulations.

Powder formulation based products typically provide a dry light feel when applied to the skin. In addition, the powder formulation may absorb skin surface moisture and/or oils and other bodily fluids, as well as deliver actives or agents to provide moisturization, odor control, lubrication, antimicrobial, and anti-irritant properties, to name a few. Typically, powder formulations comprise talc and/or corn starch alone or in combination with additional ingredients, such as fragrance, dimethicone, esters, zinc oxide, titanium dioxide, iron oxides, anti-caking agent, antioxidants, ultraviolet absorbents, etc., to provide actual or perceived benefits to the skin.

The powder formulation based products are typically applied to the skin in the form of a dusting powder or inside of an absorbent article as a dry powder form. Because these powder formulations are light, loose particles, relatively speaking, and have a relatively small particle size, application of the powder formulation may be difficult to control. Even with careful application, the powder formulations tend to form a dust cloud, causing deposits of the powder formulations over a larger area than the intended application target. Additionally, this dust cloud may cause an inhalation or aspiration health hazard, especially to young children and respiratory compromised individuals, such as those with asthma or chronic pulmonary diseases, leading to serious health situations or even death. Use of powder formulation based products by such individuals is strongly discouraged.

Cream and lotion formulation based products typically provide a smooth comfortable application as well as leaving the skin feeling moisturized or otherwise improved. While easier to use and control application of than powder formulations, the cream and lotion formulation based products may leave a wet feeling and/or greasy residue feeling on the skin or may not work well with a variety of skin types, such as oily skin.

In order to overcome the problems associated with the use of powder formulations and cream or lotion formulations, many formulators have developed liquid powder formulations that may be applied to the skin in the form a liquid, spray, and/or roll-on. However, some of the liquid powder formulations tend to dry slowly, leave a sticky or gummy feeling on the skin, during and/or after application of the formulations, or may not contain adequate amounts of powder to provide a powdery dry feeling on the skin. To reduce the transformation time of the liquid powder formulation from a liquid phase to a powder phase, the liquid powder formulations incorporate a volatile carrier into which the powder is suspended, such as an alcohol or volatile silicones or hydrocarbons. However, such volatile carriers may have a negative impact on skin health, such as dissolving or removing the natural lipid barrier of the skin, especially on compromised skin, such as chapped and chaffed skin or skin exhibiting diaper rash or dermatitis, rashes, hydration dermatitis, and other skin conditions.

Fast drying stable liquid powder formulations are needed to provide skin protection, reduced skin surface wetness and/or oiliness, lubrication and a dry powdery feel and/or appearance on the skin after application as well as providing a visual cue of skin dryness.

Accordingly, one aspect of the present invention is to provide a stable fast drying aqueous, non-alcoholic liquid powder formulation.

Another aspect of the present invention is to provide an aqueous, non-alcoholic skin protectant liquid powder formulation.

Another aspect of the present invention is to provide an aqueous, non-alcoholic liquid powder formulation that provides reduced skin surface wetness and/or oiliness after application of the formulation.

Still another aspect of the present invention is to provide an aqueous, non-alcoholic liquid powder formulation that provides a dry powdery feel and/or appearance on the skin after application of the formulation.

Still another aspect of the present invention is to provide an aqueous, non-alcoholic liquid powder formulation that provides a visual cue of skin dryness.

Still another aspect of the present invention is the application of a powder, delivered as an aqueous, non-alcoholic liquid, in a controlled manner, to provide skin protection, lubrication, a dry look, and a powdery skin feel.

These and other aspects of the present invention will become more readily apparent from consideration of the following summary and detailed description below.

SUMMARY OF THE INVENTION

Aqueous, non-alcoholic liquid powder formulations have been discovered which perceptually dries quickly leaving a silky powdery after feel and/or appearance on the skin while reducing skin surface moisture and/or oils. Such liquid powder formulations may be applied as a lotion, liquid, spray, solid, or roll-on.

The present invention relates to an aqueous, non-alcoholic liquid powder formulation that may comprise from about 20% to about 75% by weight of water, from about 25% to about 70% by weight of a powder, from about 0.05% to about 1% by weight of a polymeric emulsifier, from about 0.5% to about 15% by weight of a low molecular weight silicone, and from about 0.1% to about 10% by weight of a high molecular weight silicone. The aqueous, non-alcoholic liquid powder formulation may have an optical uniformity index of about 0.1 or less. The aqueous, non-alcoholic liquid powder formulation may have an extensive uniformity index of about 300 or greater.

In another embodiment of the present invention, the aqueous, non-alcoholic liquid powder formulation may comprise: from about 14% to about 75% by weight of water; from about 25% to about 60% by weight of a powder; from about 0.05% to about 1% by weight of a polymeric emulsifier; from about 0% to about 10% by weight of a low molecular weight silicone; from about 0% to about 5% by weight of a high molecular weight silicone; and, from about 0.1% to about 10% by weight of a solid fatty acid ester of a $C_{12}$ to a $C_{22}$ fatty acid having a melting point of about 32° C. to about 70° C.

In another embodiment of the present invention, the aqueous, non-alcoholic liquid powder formulation may have a % solids by weight of the formulation of about 30% or greater.

In still another embodiment of the present invention, the aqueous, non-alcoholic liquid powder formulation may have a percent oil and/or moisture retention value of about 0.5 grams/gram or greater.

DEFINITIONS

The term "aqueous" as used herein shall mean formulations comprising water as a volatile component and does not contain a volatile hydrocarbon or a volatile cyclomethicone.

The term "non-alcoholic" as used herein shall mean a formulation that is essentially free of ethanol or isopropyl alcohol. As used in this definition, the term "essentially" shall mean about 1% or less of the formulation shall be ethanol or isopropyl alcohol.

The term "comprising" as used herein shall mean that the formulation may contain other ingredients which are compatible with the formulation and which preferably do not substantially disrupt the formulations of the present invention. It is understood that the term encompasses the phrases "consisting of" and "consisting essentially of".

The term "moisture" as used herein shall mean the amount of water on the surface of the skin or in the stratum corneum.

The phrase "skin conditioning agent" as used herein shall mean materials that condition or moisturize the skin, including but not limited to humectants, moisturizers, exfoliants, or emollients.

The phrase "skin health agent" as used herein shall mean any material that provides skin moisturization, cleanses, reduces skin redness, protects, replenishes, nourishes, reduces cutaeneous infections, prevents oxidation, evens color or tone, improves skin elasticity, skin mechanical properties, reduces wrinkles, reduces signs of aging, improves skin topography, and/or protects from UV radiation and related sun damage.

The term "solidifying agent" as used herein shall mean the physical and/or chemical alteration of a liquid base material so as to form a solid or semi-solid at ambient conditions, i.e., to form a final formulation that has a stable physical structure and is deposited on the skin during normal use conditions.

The phrase "oil and/or moisture retention value" as used herein shall mean the amount, in grams, of oil and/or moisture that one gram of the powder has the ability to absorb/adsorb and is expressed as grams/gram.

DETAILED DESCRIPTION OF THE INVENTION

It has been unexpectedly discovered that by combining a powder with a low molecular weight silicone and a high molecular weight silicone, it is possible to produce aqueous, non-alcoholic liquid powder formulations that may be applied in the form of a spray, liquid, lotion, cream, ointment, semi-solid, solid, and/or roll-on and quickly transform to a dry powder phase, leaving a dry powdery skin feel. In addition, such liquid powder formulations may provide skin care benefits.

The aqueous, non-alcoholic liquid powder formulations of the present invention may be packaged for use to be dispensed from a container, such as a cream; a liquid or semi-liquid dispensed by squeezing the container, by a pump mechanism associated with the container, by a spray mechanism associated with the container, a roller or roll-on mechanism associated with the container; and, a solid or semi-solid dispensed from the container. The container may be a stand alone container or may be a part of or attached to a disposable absorbent article or disposable paper product. One embodiment of such a container is a pouch associated with an absorbent article.

The aqueous, non-alcoholic liquid powder formulations of the present invention may be used as a topical application or component thereof, such as lotions, sunscreens, makeup, and ointments; may comprise a component of a disposable absorbent article, such as a diaper, training pant, swim pant, adult incontinence products, feminine care products, such as menstrual pads, panty liners, tampons, and interlabial pads, and wraps; and, may comprise a component of a disposable paper product, such as facial tissue, bath tissue, wet or dry wipes or washcloths, and paper toweling.

In one embodiment of the present invention, the aqueous, non-alcoholic liquid powder formulation may comprise from about 20% to about 75% by weight of water; from about 25% to about 60% by weight of a powder; from about 0.05% to about 1% by weight of a polymeric emulsifier; from about 0.5% to about 15% by weight of a low molecular weight silicone; and, from about 0.1% to about 10% by weight of a high molecular weight silicone. The aqueous, non-alcoholic liquid powder formulation may have an optical uniformity index of about 0.1 or less. The aqueous, non-alcoholic liquid powder formulation may have an extensive uniformity index of about 300 or greater.

In another embodiment of the present invention, the aqueous, non-alcoholic liquid powder formulation may comprise from about 20% to about 75% by weight of water; from about 25% to about 60% by weight of a powder; from about 0.05% to about 1% by weight of a polymeric emulsifier; from about 0.5% to about 15% by weight of a low molecular weight silicone; and, from about 0.1% to about 10% by weight of a high molecular weight silicone.

In another embodiment of the present invention, the aqueous, non-alcoholic liquid powder formulation may have a 30% solids by weight of the formulation of about 85% or greater.

In another embodiment of the present invention, the aqueous, non-alcoholic liquid powder formulation may comprise: from about 14% to about 75% by weight of water; from about 25% to about 60% by weight of a powder; from about 0.05% to about 1% by weight of a polymeric emulsifier; from about 0% to about 10% by weight of a low molecular weight silicone; from about 0% to about 5% by weight of a high molecular weight silicone; and, from about 0.1% to about 10% by weight of a solid fatty acid ester of a $C_{12}$ to a $C_{22}$ fatty acid having a melting point of about 32° C. to about 70° C.

In another embodiment of the present invention, the aqueous, non-alcoholic liquid powder formulation may have a % solids by weight of the formulation of about 30% or greater.

In one embodiment of the present invention, the aqueous, non-alcoholic liquid powder formulation may comprise from about 20% to about 75% by weight of water; from about 25% to about 60% by weight of a powder; from about 0.05% to about 1% by weight of a polymeric emulsifier; from about 0.5% to about 15% by weight of a low molecular weight silicone; and, from about 0.1% to about 10% by weight of a high molecular weight silicone.

In another embodiment of the present invention, the aqueous, non-alcoholic liquid powder formulation may have an oil and/or moisture retention value of about 0.5 grams/gram or greater.

The aqueous, non-alcoholic liquid powder formulation may have a pH ranging from about 4 to about 8, more specifically ranging from about 4.5 to about 7, and most specifically from about 5 to about 6.

The aqueous, non-alcoholic liquid powder formulation may have a percent solids ranging from about 25 to about 90, more specifically ranging from about 30 to about 75, and most specifically from about 30 to about 60.

The aqueous, non-alcoholic liquid powder formulation may have a percent oil and/or moisture retention value ranging from about 0.1 grams/gram to about 10 grams/gram, more specifically ranging from about 0.5 grams/gram to about 8 grams/gram, and most specifically from about 1 gram/gram to about 6 grams/gram.

The aqueous, non-alcoholic liquid powder formulation may have an optical uniformity index of about 0.1 or less. The aqueous, non-alcoholic liquid powder formulation may have an extensive uniformity index of about 300 or greater.

In one embodiment of the present invention, a stable aqueous, non-alcoholic liquid powder formulation may be prepared by combining from about 24% to about 75% by weight of the formulation of water; from about 0.05% to about 1% by weight of the formulation of acrylates/$C_{10}$-$C_{30}$ alkyl acrylates; from about 0.1% to about 5% by weight of the formulation of a emulsifying surfactant or combination of surfactants having a combine HLB of about 6 to about 18; from about 25% to about 60% by weight of the formulation of a powder having a mean particle size of about 50 microns or less and selected from the group consisting essentially of talc, zinc oxide, starch, boron nitride, spray dried hydrogenated vegetable oil, non-swellable natural or organically modified clays, nylon, silicone resin powders, mixtures thereof, and the like; and, from about 0.1% to about 10% by weight of the formulation of a polysiloxane or organically modified polydimethylsiloxane:polydimethylsiloxane or organically modified gum blended in a ratio of about 1:1 to about 1:100.

In another embodiment of the present invention, a stable aqueous, non-alcoholic liquid powder formulation may be prepared by combining from about 17% to about 75% by weight of the formulation of water; from about 0.05% to about 1% by weight of the formulation of acrylates/$C_{10}$-$C_{30}$ alkyl acrylates; from about 0.1% to about 2% by weight of the formulation of an associate thickening agent selected from the group consisting essentially of carbomer, water swellable clay, cellulose or modified cellulose, modified starched, mixtures thereof, and the like; from about 0.1% to about 5% by weight of the formulation of a emulsifying surfactant or combination of surfactants having a combine HLB of about 6 to about 18; from about 25% to about 60% by weight of the formulation of a powder having a mean particle size of about 50 microns or less and selected from the group consisting essentially of talc, zinc oxide, starch, boron nitride, spray dried hydrogenated vegetable oil, non-swellable natural or synthetic clays, nylon, silicone resin powders, mixtures thereof, and the like; and, from about 0.1% to about 15% by weight of the formulation of a polysiloxane or organically modified polydimethylsiloxane:polydimethylsiloxane or organically modified gum blended in a ratio of about 1:1 to about 1:100.

In another embodiment of the present invention, a stable aqueous, non-alcoholic liquid powder formulation may be prepared by combining from about 15% to about 75% by weight of the formulation of water; from about 0.05% to about 5% by weight of the formulation of a laponite clay capable of suspending particles; from about 25% to about 60% by weight of the formulation of a powder having a mean particle size of about 50 microns or less and selected from the group consisting essentially of talc, zinc oxide, starch, boron nitride, spray dried hydrogenated vegetable oil, non-swellable natural or synthetic clays, nylon, silicone resin powders, mixtures thereof, and the like; and, from about 0.1% to about 20% by weight of the formulation of a polysiloxane or organically modified polydimethylsiloxane:polydimethylsiloxane or organically modified gum blended in a ratio of about 1:1 to about 1:100.

Low Molecular Weight Silicone

Low molecular weight silicones that may be used in the present invention conform to the general formula:

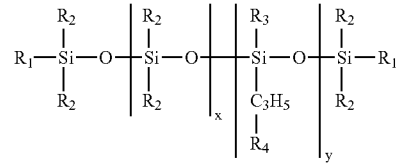

wherein, $R_1$ may be independently selected from methyl, ethyl, propyl, butyl, pentyl, hexyl, octyl ($C_1$ to $C_8$), hydroxyl, and phenyl groups;

$R_2$ may be independently selected from methyl, ethyl, propyl, butyl, pentyl, hexyl, and octyl ($C_1$ to $C_8$) groups;

$R_3$ may be selected from methyl, ethyl, propyl, butyl, pentyl, hexyl, octyl ($C_1$ to $C_8$), and trimethyl endblock groups;

$R_4$ may be selected from methyl, ethyl, propyl, butyl, pentyl, hexyl, octyl (caprylyl), dodecyl, lauryl, cetyl or stearyl, phenyl, amino, ether, and vinyl groups; and, x is about 0 to about 100 and y is about 0 to about 15.

The average molecular weight of the low molecular weight silicone may be about 10,000 or less, more specifically ranging from about 100 to about 10,000, more specifically ranging from about 200 to about 8,000, and most specifically ranging from about 300 to about 6,000. The average viscosity of the low molecular weight silicone ranges from about 0.65 centipose to about 350 centipose; more specifically from about 5 centipose to about 200 centipose; and, more specifically from about 10 centipose to about 100 centipose.

Examples of low molecular weight silicones that may be used in the present invention include, but is not limited to: dimethicone (0.65 cSt to 200 cSt); amodimethicone; simethicone; hexamethylsiloxane; steroxytrimethylsilane; vinyldimethicone; divinyldimethicone; phenyl propyl trimethicone; diphenylmethicone; phenyl trimethicone; trisiloxane; trimethicone; caprylyl trimethicone; hexymethicone; caprylyl methicone; lauryl methicone; mixtures thereof; and, the like.

The amount of the low molecular weight silicone that may be incorporated into the aqueous, non-alcoholic liquid powder formulation may range from about 0.5% to about 15% by weight of the formulation, more specifically from about 1% to about 13% by weight of the formulation, and most specifically from about 5% to about 10% by weight of the formulation.

High Molecular Weight Silicone

High molecular weight silicones that may be used in the present invention include, but are not limited to: dimethicone gum; dimethiconol gum; silicone elastomers; acrylates/dimethicone methacrylate copolymers; PEG-12 dimethicone crosspolymer; divinyldimethicone/dimethicone Crosspolymer; nylon-611/Dimethicone; mixtures thereof; and, the like.

The average molecular weight of the high molecular weight silicone may be about 100,000 or greater, more specifically ranging from about 100,000 to about 10,000,000, more specifically ranging from about 250,000 to about 5,000,000, and most specifically ranging from about 500,000 to about 3,000,000.

Examples of high molecular weight silicones that may be used in the present invention include, but is not limited to, dimethicone/vinyl dimethicone crosspolymer, commercially available under the trade designation of Dow Corning 9506 Cosmetic Powder from Dow Corning Corporation, located at 1100 Salzburg Rd, Midland, Mich., 48686, and dimethicone available under the trade designation SE 30 from General Electric, located in Waterford, N.Y., 12188.

These high molecular weight silicones have such a high molecular weight they may be difficult to process and may require specialized mixing equipment. However, many of these high molecular weight silicones are commercially sold as blends with low molecular weight silicones or other solvent and/or as emulsions/suspensions. Examples of such blends of high and low molecular weight silicones include, but are not limited to: Dow Corning 1401 (cyclomethicone and dimethiconol); Dow Corning 1403 (cyclomethicone and dimethiconol); Dow Corning 1404 (dimethicone and dimethiconol); Dow Corning 1411 (cyclomethicone and dimethicone); Dow Corning 1413 (dimethicone); Dow Corning 1428 (dimethicone); Dow Corning 1503 (dimethicone and dimethiconol); Dow Corning 2-8178 (Nylon-611/dimethicone and PPG-3 myristyl ether); Dow Corning 9010 (cyclopentasiloxane and PEG-12 dimethicone crosspolymer); Dow Corning 9040 (cyclomethicone and dimethicone crosspolymer); Dow Corning 9042 (cyclomethicone and dimethicone crosspolymer); mixtures thereof; and, the like. Examples of emulsion/suspensions include, but are not limited to: Dow Corning 9090 (divinyldimethicone/dimethicone crosspolymer and PPG-1-deceth-6); Dow Corning BY29-119; Dow Corning 9509; mixtures thereof; and, the like.

In one embodiment of the present invention, a blend comprising a low molecular weight silicone and high molecular weight silicone may provide a deposition of a fine film of the high molecular weight silicone, such as 1 to 10 monolayers. This monolayer film structure may provide a non-sticky film which to the user feels silky and powdery.

Small amounts of medium molecular weight silicones may be added to the aqueous, non-alcoholic liquid powder formulations as long as the presence of the medium molecular weight silicones have no effect on the aesthetic feel of the liquid powder formulations, such as causing a sticky or gummy skin feel. The average molecular weight of the medium molecular weight silicones ranges from between about 10,000 and about 100,000.

The amount of the high molecular weight silicone that may be incorporated into the aqueous, non-alcoholic liquid powder formulation may range from about 0.1% to about 10% by weight of the formulation, more specifically from about 0.5% to about 7% by weight of the formulation, and most specifically from about 1% to about 5% by weight of the formulation.

The ratio of the low molecular weight silicone to high molecular weight silicone that may be incorporated into the aqueous, non-alcoholic liquid powder formulation may range from about 10:1 to about 1:1, more specifically from about 8:1 to about 2:1, and most specifically from about 6:1 to about 4:1.

Solid Fatty Acid Ester

Solid fatty acid ester of a $C_{12}$-$C_{22}$ fatty acid that may be used in the present invention may have a metling point of about 32° C. to about 70° C. include, but are not limited to: myristyl myrisate; stearyl benzoate; behenyl benzoate; stearyl behenate; behenyl behenate; cetyl lactate; stearyl lactate; $C_{12}$-$C_{15}$ alkyl lactate; myristyl lactate; cetearyl stearate; cetearyl palmitate; cetyl esters; mixtures there of; and, the like.

Polymeric Emulsifier

Polymeric emulsifiers that may be used in the present invention include, but are not limited to: acrylates/alkyl acrylates crosspolymers; acrylates/acryamide acrylates copolymers; mixtures thereof; and, the like.

Examples of polymeric emulsifers that may be used in the present invention include, but are not limited to: acrylate/alkyl acrylate crosspolymers sold under the trade designation of Pemulen and Carbopol ETD polymers by Noveon, Inc., located at 9911 Brecksville Road, Cleveland, Ohio, 44141; acrylate/acrylamide copolymers sold under the trade designation of Novemer by Noveon, Inc.; hydroxypropyl starch phosphate sold under the trade designation of Structure XL by National Starch and Chemical Company, located at Finderne Avenue, Bridgewater, N.J., 08807; mixtures thereof; and, the like. Some examples of such crosspolymers and copolymers include, but are not limited to: acrylate/$C_{10}$-$C_{30}$ alkyl acrylate crosspolymers; acrylate/acrylamide copolymers; hydroxypropyl starch phosphate; mixtures thereof; and, the like.

The amount of the polymeric emulsifier that may be incorporated into the aqueous, non-alcoholic liquid powder formulation may range from about 0.05% to about 1% by weight of the formulation, more specifically from about 0.1% to about 0.5% by weight of the formulation, and most specifically from about 0.12% to about 0.15% by weight of the formulation.

A co-emulsifier may be also incorporated into the aqueous, non-alcoholic liquid powder formulation. Examples of co-emulsifers that may be used in the present invention include, but are not limited to: sorbitan sesquioleate; sorbitan trioleate; glyceryl stearate; polyoxyethylene 2 lauryl ether; polyoxyethylene 2 cetyl ether; polyoxyethylene 2 stearyl ether; polyoxyethylene 2 oleyl ether; polyoxyethylene 20 sorbitan monolaurate; polyoxyethylene 60 sorbitan monostearate; mixtures thereof; and, the like.

The amount of the co-emulsifier that may be incorporated into the aqueous, non-alcoholic liquid powder formulation may range from about 0.1% to about 10% by weight of the formulation, more specifically from about 1% to about 8% by weight of the formulation, and most specifically from about 2% to about 5% by weight of the formulation.

The co-emulsifier may have a hydrophilic/lipophilic balance value ranging from about 4 to about 14, more specifically ranging from about 6 to about 12, and most specifically ranging from about 8 to about 11. The HLB is a numeric rating system for the combined hydrophilic and lipophilic characteristics of an amphiphilic molecule that contains both hydrophilic and lipophilic moieties, and thus is a measure of the emulsifying efficiency of an emulsifier. The HLB is related to the polarity of the molecule, the least hydrophilic emulsifiers having low HLB values, and increasing number correspond to increasing hydrophilic characteristics of emulsifiers. The specific HLB value that may be applied in the present invention is dependent on the hydrophobic material or skin health active being emulsified into the liquid powder formulation of the present invention.

The assignment of numerical values for HLB based upon chemical groupings in a molecule is given in "Physical Chemistry of Surfactants," $2^{nd}$ Ed. by A. W. Adamson (Interscience Publishers, New York 1967), pp. 520-522. A definition of HLB is also provided in Volume 1 of the Surfactants Science Series, Nonionic Surfactants, Chapter 18 by M. J. Schnick (M. Dekker Inc., New York 1967).

Powder

Powders that may be used in the present invention include, but are not limited to: talc; chemically treated talc; corn starch; potato starch; tapioca starch; rice starch; root starch; pea starch; sweet potato starch; amaranth; banana starch; sorghum; barley flour; wheat flour; oat starch; rye starch; modified starches, such as starch octenylsuccinate, hydroxypropylated di-starch phosphates, and thermally inhibited starch; oatmeal; titanium dioxide; treated titanium dioxide; zinc oxide; treated zinc oxide; iron oxide; treated iron oxide; boron nitride; fluorcarbon powder; polytetrafluoro-ethylene powder; chlorotrifluro-ethylene-ethylene powder; cellulose propionate powder; cellulose acetate butyrate powder; cellulose acetate; spray-dried vegetable oil; shea butter powder; menthylpentene polymer powder; ethyl cellulose powder; acetal homopolymer powder; acrylic polymer powder; cellulose nitrate powder; polypropylene powder; polyallomer powder; polybutylene powder; inonmer polymer powder; polyethylene powder; nylon powder; polyamide powder; acylics multipolymer powder; styrene butadiene thermoplastic powder; polyvinylchloride powder; nylon (polyamide) powder; urea formaldehyde powder; styrene acrylonitrile copolymer; polystyrene powder; polycarbonate; polysulfone powder; non-swellable natural and/or synthetic clays; kaolin; mica; sulfer; organically modified clays; non-solubilized silicone resin powder; non-solubilized PEG-12 dimethicone crosspolymer powder; non-solubilized dimethicone crosspolymer powder; non-solubilized divinyldimethicone/dimethicone copolymer; mixtures thereof; and, the like. The powders may be presented in the form of microcapsules, and the like.

The powders that may be used in the present invention are not restricted by shape. They may be spherical, acicular, plate-like, tabular, or amorphous in structure. Typically, powders comprising particles having plate-like structures are used. The powders may be porous or non-porous. The particle size of the particles of the powders that may be used in the present invention may be about 70 microns or less, more specifically about 50 microns or less, and more specifically about 20 microns or less in diameter. The particles of the powder may range in mean particle size from about 0.9 microns to about 70 microns, more specifically from about 1 microns to about 50 microns, and most specifically from about 10 microns to about 30 microns.

Selection of the powder may determine the optical properties of the surface of the skin treated by the liquid powder formulation. The visual perception of the skin surface after the application of the liquid powder formulation may be altered by the selection of a powder having the appropriate size and shape of the particles to provide the desired optical properties to be realized on the surface of the skin treated with the liquid powder formulation. The particles of powder having irregular shapes may provide an optical perception of dryness of the surface of skin after an application of a liquid powder formulation comprising such particles. Mixing powders comprising particles of different refractive indices may further alter the optical perception of the treated skin surface.

Table 1 provides refractive indexes of powders that may be used in the present invention. The refractive index for a given powder is the ratio of the velocity of light in a vacuum to its velocity within the powder. It is also the ratio of the sine of the angle of incidence to the sine of the angle of refraction. The light that is not refracted into the given powder will either be absorbed by the powder or reflected off the surface of the powder. Using particles having a higher refractive index than the refractive index of the skin to be treated may result in more refracted light, less reflected light, and a better perception of skin dryness.

Altering the reflection of light from the surface of the skin may be accomplished by the selection of the powder incorporated into the liquid powder formulation. Particles of powder having irregular shapes typically scatter larger amounts and reflect smaller amount of the incident light than regular shaped particles of powder, such as spherical shaped particles. The reaction of the irregularly shaped particles of powder to incident light translates into a less shiny, more matte appearing surface of the skin treated with the powder.

Particles with irregular shapes would be preferred over spherical particles for delivering visual dryness perception. Irregular particles would scatter larger amounts and reflect smaller amounts of the incident light which translates into perception of less shiny and more matte surface for the human eye. In some embodiments of the present invention, the size of the particles would be small enough to avoid the gritty feel of individual particles. Particles below 50 microns, and more typically below 20 microns, are usually too small to be perceived as gritty.

TABLE 1

Refractive Indexes of Various Powders

| | |
|---|---|
| Fluorcarbon (FEP) | 1.34 |
| Polytetrafluoro-Ethylene (TFE) | 1.35 |
| Chlorotrifluoro-Ethylene (CTFE) | 1.42 |
| Cellulose Propionate | 1.46 |
| Cellulose Acetate Butyrate | 1.46-1.49 |
| Cellulose Acetate | 1.46-1.50 |
| Methylpentene Polymer | 1.48 |
| Ethyl Cellulose | 1.47 |
| Acetal Homopolymer | 1.48 |
| Acrylics | 1.49 |
| Cellulose Nitrate | 1.49-1.51 |
| Polypropylene (Unmodified) | 1.49 |
| Polyallomer | 1.49 |
| Polybutylene | 1.50 |
| Ionomers | 1.51 |
| Polyethylene (Low Density) | 1.51 |
| Nylons (PA) Type II | 1.52 |
| Acrylics Multipolymer | 1.52 |
| Polyethylene (Medium Density) | 1.52 |
| Styrene Butadiene Thermoplastic | 1.52-1.55 |
| PVC (Rigid) | 1.52-1.55 |
| Nylons (Polyamide) Type 6/6 | 1.53 |
| Urea Formaldehyde | 1.54-1.58 |
| Polyethylene (High Density) | 1.54 |
| Styrene Acrylonitrile Copolymer | 1.56-1.57 |
| Polystyrene (Heat & Chemical) | 1.57-1.60 |
| Polycarbornate (Unfilled) | 1.586 |
| Polystyrene (General Purpose) | 1.59 |
| Polysulfone | 1.633 |

The refractive index of the surface of skin is about $n=1.47$ and about $n=1.40$ in the stratum corneum and about $n=1.39$ at the dermis. (See W. Knaak, S. Bonev, and A. Knuttl, New Method for Evaluation of In Vivo Scattering and Refractive Index Properties Obtained with Optical Coherence Tomography, Journal of Biomedical Optics, Vol. 9(20, pp. 265-273 (2004). The higher the moisture content of the skin or its components, the refractive index values decrease.

By altering the size and shape of the particles of the powder, the skin feel provided by the liquid powder formulation may be devised to provide the desired sensory queue for dryness, skin tone, skin smoothness, and the like.

The surface of skin may appear wet when it is oily. The use of oil absorbing powders may be used in the present invention to remove excess oil and/or moisture from the skin surface and, thereby rendering a healthier and drier appearance of the skin surface. Microspheres and/or ellipsoids have been found to provide good skin appearance as well as skin feel due to efficient moisture and/or oil absorption.

Microspheres and/or ellipsoids are capable reducing the shiny look of moisture and/or oil due to their light scattering properties as well as absorption properties. For tactile perception, microspheres and/or ellipsoids may act as a barrier between the fingers and the oily and/or moist surface of the skin. Microspheres and/or ellipsoids may be capable of absorbing up to seven times their weight in moisture and/or oil due to their porous surface and accessible inner void.

The microspheres and/or ellipsoids may be preloaded with a volatile material, such as water, cyclomethicone, volatile hydrocarbons, and the like, so that the volatile material evaporates when applied on the surface of the skin, leaving the microspheres and/or ellipsoids empty and ready to absorb skin surface moisture and/or oils.

The microspheres and ellipsoids that may be used in the present invention include, but are not limited to: ZELEC Sil (commercially available from Du Pont, located at 1007 Market Street, Wilmington, Del., 19898); MSS-500, MSS-500/3, MSS-500H, MSS-500/3H and MSS-500/3H4, MSS-500N, and MSS-500/3N (commercially available from Kobo Products Inc., located at 690 Montrose Avenue, South Plainfield, N.J., 07080); Spheron L1500 and Spheron P1500 (commercially available from Presperse Inc., located at 635 Pierce Street, Somerset, N.J., 08873); Microsponges and Polytrap (commercially available from Cardinal Health, located at 7000 Cardinal Place, Dublin, Ohio, 43017); Aerosil (commercially available from Degussa, located at 379 Interpace Parkway, Parsippany, N.J., 07054); Cab-O-Sil (commercially available from Cabot Corporation, located at 700 E. U.S. Highway 36, Tuscola, Ill., 61953). Starches and modified starches may also be used to absorb moisture and/or oils from the surface of the skin and/or mitigate greasiness of the aqueous, non-alcoholic liquid powder formulations. Examples include tapioca starch, aluminum starch octenylsuccinate, and modified corn starch (commercially available from National Starch and Chemical Company, located at 10 Finderne Avenue, Bridgewater, N.J., 08807). The same techniques may be used when the source of the oily perception is not skin oils but rather an oily formulation that is applied directly on the skin or indirectly through transfer from articles that contact the surface of the skin (e.g. absorbent articles).

Powdered microcapsules may be used in aqueous, non-alcoholic liquid powder formulation of the present invention to deliver a variety of additional ingredients and/or benefits, such as skin health benefits. The additional ingredients, such as skin health agents, for example, may be encapsulated in a number of shell materials including but not limited to liposomes, nanosomes, nanoparticles, collagen, gelatin, dextrin, melamine resin, silicone resin, and starch. The advantages of having the additional ingredients encapsulated are many and well know in the art but the major advantages are protecting the active ingredient from exposure to harsh environmental conditions (oxidation), separating incompatible ingredients, and most advantageously controlling the release of the additional ingredients during or after the application of the aqueous, non-alcoholic liquid powder formulation. Controlled release may be triggered release, sustained release, or a combination, where the additional ingredient is released form the shell material or the entrapment material by a number of mechanisms including, but not limited to pressure, pH, UV light, capillary forces, and wetting with water. The particle size of microencapsulated materials and the polymeric entrapment materials typically have a size from about 0.1 micrometers to about 40 micrometers, preferably from about 0.3 micrometers to about 20 micrometers, more preferably from about 0.5 micrometers to about 15 micrometers.

The amount of the powder that may be incorporated into the aqueous, non-alcoholic liquid powder formulation may range from about 25% to about 60% by weight of the formulation, more specifically from about 30% to about 50% by weight of the formulation, and most specifically from about 35% to about 40% by weight of the formulation.

Neutralizing Base

The pH of the aqueous, non-alcoholic liquid powder formulation may be adjusted by the introduction of a neutralizing base. As stated above, the pH of the aqueous, non-alcoholic liquid powder formulation may range between about 4 to about 8.

Neutralizing bases that may be used in the present invention include, but are not limited to: triethanolamine; sodium hydroxide; ammonium hydroxide; sodium borate; sodium citrate; aminomethylpropanol (AMP); mixtures thereof; and, the like.

Water

The amount of water that may be incorporated into the aqueous, non-alcoholic liquid powder formulation may range from about 14% to about 75% by weight of the formulation, more specifically from about 20% to about 75%, more specifically from about 40% to about 65% by weight of the formulation, and most specifically from about 45% to about 55% by weight of the formulation.

Additional Ingredients

The aqueous, non-alcoholic liquid powder formulation of the present invention may include one or more additional ingredients. Such ingredients may improve a quality of the liquid powder formulation itself, a benefit delivered by the liquid powder formulation, processability of the liquid powder formulation, or a combination thereof. Additional ingredients that may be used in the present invention include, but are not limited to: antifoaming agents; antimicrobial actives; anti-inflammatory agents; antifungal actives; antiviral actives; antiseptic actives; antioxidants; astringents; biological actives; colorants, deodorants; emollients; humectants; exfoliants; fatty alcohols; film formers; fragrances; fragrance solubilizers; lubricants; anti-caking agents; medicants; buffers; natural moisturizing agents; skin health agents; skin conditioning agents; skin protectants; solvents; solubilizing agents; suspending agents; surfactants; antiperspirants; abrasives; wetting agents; ultraviolet absorbing agents; sunscreens, organic and inorganic; thickening agents; solidifying agents; preservatives; combinations thereof; mixtures thereof; and, the like.

The amount of the additional ingredient or ingredients that may be incorporated into the aqueous, non-alcoholic liquid powder formulation may range from about 0.01% to about 15% by weight of the formulation, more specifically from about 0.1% to about 10% by weight of the formulation, and most specifically from about 1% to about 5% by weight of the formulation. However, it is understood that the actual amount of any given additional ingredient incorporated into the aqueous, non-alcoholic liquid powder formulation will depend upon the additional ingredient itself and the desired effect of that additional ingredient on the liquid powder formulation or to be delivered by the liquid powder formulation.

EXAMPLES

Testing Procedure

Uniformity Factor

Method
1. Cut an 8 cm×27.5 cm strip of PP2500 transparency film (hereinafter referred to as the "first strip"). The PP2500 transparency film is commercially available from 3M, located in St. Paul, Minn.
2. Draw two parallel lines using a Sharpie® fine point permanent marker (commercially available from Sanford, located in Chicago, Ill.) on the first strip at 1.5 cm and 7.5 cm, respectively, from the back-end of the first strip such that the lines are perpendicular to the direction of travel of the first strip as discussed in Steps 6 and 7.
3. Coat a 40 mm×40 mm×0.85 mm layer of the test formulation, centering the coating between the two parallel lines marked on the first strip in Step 2.
4. Attach first strip coated with the test formulation to the base of a Monitor & Slip and Friction apparatus (commercially available from TMI, located in Amityville, N.Y.), placing the first strip such that the side coated with the test formulation is facing upward.
5. Cut a 6 cm×6 cm strip of PP2500 transparency film (hereinafter referred to as the "second strip"). Attach the second strip to the bottom of a 97.72 gram TMI sled using a double sided tape.
6. Set the Monitor & Slip and Friction apparatus for a total pull distance of 19.0 cm at a speed of 15 mm/min.
7. Place the TMI sled on the top of the first strip such that the second strip attached to the bottom of the TMI sled is in contact with the coating of the test formulation on the first strip. Center the TMI sled between the parallel lines drawn on the first strip. Allow the TMI sled to pull along the first strip for 19.0 cm at 15 mm/min.
8. Remove the first strip and place in a 5VY811 heavy duty clear vinyl sheet protector with a black backing (commercially available from Avery, located in Brea, Calif.).
9. Collect images with a HP Scan Jet 5470C (commercially available from Hewlett-Packard Company, located in Palo Alto, Calif.) with automatic options turned off. All images of the test formulation on the first strip are taken beside a Kodak Gray Scale standard (commercially available from Kodak CYM, located in New York, N.Y.) as the reference.
10. Analyze the images of the test formulation on the first strip using the Metamorph image analysis software (commercially available from Universal Image, located in Downingtown, Pa.). The images are analyzed using a threshold value set at the 11-12 interface of the Kodak Grey Scale standard. All objects within the images with a pixel area below 2500 were rejected.

TABLE 2

Test materials

| Product | Lot | Manufacture | Location | Code Label |
|---|---|---|---|---|
| Johnson Baby Powder | 0224RB | Johnson & Johnson | Skillman, NJ | J&J Powder |
| Baby Liquid Talc | 317728 | Avent | Suffolk, CO | Avent LP |
| Liquid Powder with Aloe&E | PX5-070604 | Kimberly-Clark | Neenah, WI | KC LP |

Image Measurement Definitions as Used Herein:

Pixel Area: The number of pixels in the object.

Texture Difference Moment (TDM): TDM is a measure of the uniformity of the gray levels in an object. Objects with uniform gray level will have a texture difference moment (TDM) close to 0. Objects with greater variation of gray level will have a larger TDM value.

The Markov texture parameters (Pressman, J. Histochem. Cytochem. 24:138, 1976) are calculated as the sum of the elements of a weighted conditional gray level transition probability matrix. Larger weights are assigned to elements far from the matrix diagonal. $P_L(i/j)$ is the conditional probability of gray level I occurring L pixels away after gray level j occurs, where L is defined as the step size. N is the number of gray levels in the object. N=8 because the object gray levels are reassigned by histogram equalization into 8 bins.

$$TDM = \sum_{i=}^{N} \sum_{j=}^{N} (i-j)^2 P_L(i/j)$$

$$ODV = \frac{\sum_{i,j} (OD^{i,j} - MOD)^2}{(N-1)(MOD)^2}$$

$MOD$ = mean optical density $OD = \text{Log}_{10}(1/\text{transmittance})$ $$\text{Transmittance} = \frac{\text{transmitted light}}{\text{incident light}}$$

Optical Density (OD): The inverse logarithm of the grayscale transmittance, where the transmittance at a given pixel is considered to be its grayscale value divided by the maximum possible number of grayscale levels (e.g. 256 for an 8-bit image)

OD Variance (ODV): A measure of the OD distribution in an object. For objects of very uniform density, the variance approaches 0. The variance approaches a maximal value of 1.0 for objects with greater contrast.

Optical Uniformity Index (OUI): Optical Uniformity Index (OUI)=TDM×ODV

Extensive Uniformity Index (EUI):

Extensive Uniformity Index (EUI)=((TDM×ODV)/Pixel Area))/1000

Results

TABLE 2

Averaged values for liquid powder and powder mixture. (n = 4)

| Product | Pixel Area | Texture Difference Moment (TDM) | OD Variance (ODV) |
|---|---|---|---|
| J&J Powder | 200819 | 1.09 | 0.11 |
| Avent LP | 292413 | 0.59 | 0.20 |
| KC LP | 311896 | 0.53 | 0.16 |

TABLE 3

| | Uniformity Indexes | |
|---|---|---|
| Product | Optical Uniformity Index (OUI) | Extensive Uniformity Index (EUI) |
| J&J Powder | 0.12 | 167 |
| Avent LP | 0.12 | 244 |
| KC LP | 0.08 | 370 |

The impact of overall mixture uniformity on formulation function is critical for optimum product performance and consumer satisfaction. The more uniform the formulation the easier the use and control of mixture with regard to application to the skin. Furthermore, formulation uniformity drives the ability of a mixture to provide a smooth and comfortable feel to the skin.

For the described liquid powder formulations there are two indexes of uniformity that help define the overall quality or state of being unvarying when applied to the skin. The Optical Uniformity Index (OUI) is a measure of the freedom from variation with regard to texture and optical quality. The Extensive Uniformity Index (EUI) is a measure of the combined optical and texture characteristics as related to the ability of the formulation to spread on the skin. The lower the OUI value the more uniform the formulation. The higher the EUI value the more uniform the formulation. The most consumer preferred formulation may have both a low OUI and a high EUI.

An aqueous, non-alcoholic liquid powder formulation of the present invention may have an OUI value of about 0.1 or less, or more specifically about 0.08 or less. In other embodiments of the present invention, the aqueous, non-alcoholic liquid powder formulation of the present invention may have an OUI value of about 0.1 to about 0, more specifically about 0.1 to about 0.001, and more specifically about 0.08 to about 0.01.

An aqueous, non-alcoholic liquid powder formulation of the present invention may have an EUI value of about 300 or greater, more specifically about 370 EUI or greater. In other embodiments of the present invention, the aqueous, non-alcoholic liquid powder formulation of the present invention may have an EIO value of about 300 to about 100,000, more specifically about 350 to about 10,000, and more specifically about 370 to about 1,000.

In one embodiment of the present invention, the aqueous, non-alcoholic liquid powder formulation may have an OUI value of about 0.1 or less and an EUI value of about 300 EUI or greater. In another embodiment of the present invention, the aqueous, non-alcoholic liquid powder formulation may have an OUI value of about 0.1 or less and an EUI value of about 370 or greater. In another embodiment of the present invention, the aqueous, non-alcoholic liquid powder formulation may have an OUI value of about 0.08 or less and an EUI value of about 300 or greater. In another embodiment of the present invention, the aqueous, non-alcoholic liquid powder formulation may have an OUI value of about 0.08 or less and an EUI value of about 370 or greater.

Examples of Aqueous, Non-Alcoholic Liquid Powder Formulations

| Ingredient | Ex. 1 wt % | Ex. 2 wt % | Ex. 3 wt % | Ex. 4 wt % | Ex. 5 wt % | Ex. 6 wt % |
|---|---|---|---|---|---|---|
| Water | 52 | 62.4 | 65.5 | 60.45 | 54.05 | 36.47 |
| PEG 9 Dimethicone | | 1 | | | | |
| Dimethicone 10 cSt | 2 | 1 | | | 10 | 1 |
| Dimethicone 100 cSt | 2 | 5 | | | | |
| Caprylyl trimethicone | | | | 2 | | |
| Phenyl trimethicone | | | | 2 | | |
| Dimethicone and Dimethiconol (Dow Corning 1403) | 2 | 3 | | | | 1 |
| Dimethicone and Dimethiconol (Dow Corning 1401) | | | | | 8 | |
| Nylon-611/Dimethicone | | | | 2 | | |
| Dimethicone/vinyl dimethicone crosspolymer | | | | | 2 | |
| Myristyl Myristate | | | 2 | | | |
| Stearyl Benzoate | | | 2 | 1 | | |
| Cetyl Lactate | | 1 | 2 | | | |
| Acrylates/C10-30 Alkyl Acrylate Crosspolymer | 0.25 | 0.2 | 0.15 | 0.5 | 0.3 | 0.25 |
| Fragrance | 0.15 | 0.15 | 0.3 | 0.2 | 0.1 | 0.15 |
| Preservative (Propylene Glycol, DMDM Hydantoin, methyl paraben and propyl paraben) | 0.75 | 0.5 | 0.5 | 0.6 | 0.5 | 0.5 |
| Disodium EDTA | 0.05 | 0.05 | 0.05 | 0.05 | 0.05 | 0.05 |
| Zea Mays (Corn) Starch | 40 | | 15 | 30 | | |
| Tapioca Starch | | 25 | | | 25 | |
| Starch Octenylsuccinate | | | 10 | | | 60 |
| Boron Nitride | | | 2 | | | 0.5 |
| Sodium Borate | 0.8 | 0.7 | 0.5 | 1.2 | 0.5 | 0.8 |

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An aqueous, non-alcoholic liquid powder formulation comprising:
   (a) from about 14% to about 75% by weight of the formulation of water;
   (b) from about 25% to about 60% by weight of the formulation of a powder;
   (c) from about 0.05% to about 1% by weight of the formulation of a polymeric emulsifier;
   (d) from about 0.5% to about 15% by weight of the formulation of a low molecular weight silicone wherein the low molecular weight silicone has an average molecular weight of 10,000 or less;
   (e) from about 0.1% to about 10% by weight of the formulation of a high molecular weight silicone wherein the high molecular weight silicone has an average molecular weight of 100,000 or greater,
wherein the liquid powder formulation has a percent solids of greater than 30%; and
wherein the liquid powder formulation has an OUI of 0.1 or less.

2. The aqueous, non-alcoholic liquid powder formulation of claim 1, further comprising from about 0.1% to about 10% by weight of the formulation of a solid fatty acid ester of a $C_{12}$ to $C_{22}$ fatty acid having a melting point of about 32° C. to about 70° C.

3. The aqueous, non-alcoholic liquid powder formulation of claim 1, wherein the weight percent of the formulation of the water is from about 20% to about 75%.

4. The aqueous, non-alcoholic liquid powder formulation of claim 1, wherein the liquid powder formulation has an EUI of about 300 or greater.

5. The aqueous, non-alcoholic liquid powder formulation of claim 1, further comprising an additional ingredient selected from the group consisting essentially of fragrances, fragrance solubilizers, colorants, skin health agents, preservatives, and mixtures thereof.

6. The aqueous, non-alcoholic liquid powder formulation of claim 5, wherein the skin health agent is selected from the group consisting essentially of antimicrobial actives, anti-inflammatory agents, antifungal actives, antiviral actives, antiseptic actives, antioxidants, astringents, biological actives, deodorants, emollients, humectants, exfoliants, natural moisturizing agents, skin conditioning agents, skin protectants, antiperspirants, ultraviolet absorbing agents, sunscreens, phytosterols, vitamins, botanicals, and mixtures thereof.

7. The aqueous, non-alcoholic liquid powder formulation of claim 6, wherein the skin health agent is a sunscreen.

8. The aqueous, non-alcoholic liquid powder formulation of claim 1, wherein the powder is selected from the group consisting essentially of starches, modified starches, boron nitride, spray dried hydrogenated vegetable oils, oatmeal, titanium dioxide, treated titanium dioxide, zinc oxide, treated zinc oxide, shea butter powder, polyethylene powder, nylon powder, polyamide powder, acylics multipolymer powder, nylon (polyamide) powder, non-swellable natural and/or synthetic clays, organically modified clays, non-solubilized silicone resin powder, non-solubilized PEG-12 dimethicone crosspolymer powder, non-solubilized dimethicone crosspolymer powder, non-solubilized divinyldimethicone/dimethicone copolymer, microcapsules, and mixtures thereof.

9. The aqueous, non-alcoholic liquid powder formulation of claim 8, wherein the powder is corn starch.

10. The aqueous, non-alcoholic liquid powder formulation of claim 8, wherein the powder is tapioca starch.

11. The aqueous, non-alcoholic liquid powder formulation of claim 8, wherein the powder is oatmeal.

12. The aqueous, non-alcoholic liquid powder formulation of claim 8, wherein the powder is a microcapsule.

13. The aqueous, non-alcoholic liquid powder formulation of claim 12, wherein the microcapsule comprises a shell material selected from the group comprising collagen, gelatin, dextrin, melamine resin, silicone resin, and starch.

14. The aqueous, non-alcoholic liquid powder formulation of claim 12, wherein the microcapsule comprises a core material of a skin health benefit agent.

15. The aqueous, non-alcoholic liquid powder formulation of claim 1, wherein the low molecular weight silicone is selected from the group consisting essentially of d imethicone, amodimethicone, simethicone, hexamethylsiloxane, steroxytrimethylsilane, vinyldimethicone, divinyldimethicone, phenyl propyl trimethicone, diphenylmethicone, phenyl trimethicone, trisiloxane, trimethicone, caprylyl trimethicone, hexymethicone, caprylyl methicone, lauryl methicone, and mixtures thereof.

16. The aqueous, non-alcoholic liquid powder formulation of claim 15, wherein the low molecular weight silicone is dimethicone.

17. The aqueous, non-alcoholic liquid powder formulation of claim 1, wherein the high molecular weight silicone is selected from the group consisting essentially of dimethicone gum, dimethiconol gum, silicone elastomers, acrylates/dimethicone methacrylate copolymers, PEG-12 dimethicone crosspolymer, divinyldimethicone/dimethicone crosspolymer, nylon-611/dimethicone, and mixtures thereof.

18. The aqueous, non-alcoholic liquid powder formulation of claim 17, wherein the high molecular weight silicone is dimethiconol gum.

19. The aqueous, non-alcoholic liquid powder formulation of claim 17, wherein the high molecular weight silicone is dimethicone gum.

20. The aqueous, non-alcoholic liquid powder formulation of claim 1, wherein the polymeric emulsifier is selected from the group consisting essentially of acrylates/alkyl acrylates crosspolymers; acrylates/acrylamide acrylates copolymers, and mixtures thereof.

21. The aqueous, non-alcoholic liquid powder formulation of claim 20, wherein the polymeric emulsifier is acrylates/$C_{10}$-$C_{30}$ alkyl acrylates crosspolymers.

22. The aqueous, non-alcoholic liquid powder formulation of claim 20, wherein the polymeric emulsifier is acrylates/acrylamide acrylates copolymer.

23. The aqueous, non-alcoholic liquid powder formulation of claim 1, wherein the weight percent of the formulation of the powder is from about 30% to about 50%.

24. The aqueous, non-alcoholic liquid powder formulation of claim 1, wherein the powder has a mean particle size of about 70 microns or less.

25. The aqueous, non-alcoholic liquid powder formulation of claim 1, further comprising a neutralizing agent.

26. The aqueous, non-alcoholic liquid powder formulation of claim 25, wherein the neutralizing agent is selected from the group consisting essentially of triethanolamine, sodium hydroxide, sodium borate, sodium citrate, and mixtures thereof.

27. The aqueous, non-alcoholic liquid powder formulation of claim 1, wherein the aqueous, non-alcoholic liquid powder formulation has a pH of about 4 to about 8.

28. The aqueous, non-alcoholic liquid powder formulation of claim 1, wherein the aqueous, non-alcoholic liquid powder formulation has a percent oil and/or moisture retention value of about 0.5 grams/gram to about 8 grams/gram.

29. The aqueous, non-alcoholic liquid powder formulation of claim 1, wherein the aqueous, non-alcoholic liquid powder formulation is a component of a disposable article or a disposable paper product.

30. The aqueous, non-alcoholic liquid powder formulation of claim 1, wherein the aqueous, non-alcoholic liquid powder formulation is packaged as a lotion to be delivered to the skin in the form from the group comprising squeezable from a container, pumpable from a container, sprayable from a container, spreadable from a roll-on container, dispensable from a container, and dispensable from a container component of a disposable article or paper product.

31. The aqueous, non-alcoholic liquid powder formulation of claim 1, wherein the aqueous, non-alcoholic liquid powder formulation is in the form of an emulsion stick.

32. An aqueous, non-alcoholic liquid powder formulation comprising:
(a) from about 14% to about 75% by weight of the formulation of water;
(b) from about 25% to about 60% by weight of the formulation of a powder;
(c) from about 0.05% to about 1% by weight of the formulation of a polymeric emulsifier;
(d) from about 0.5% to about 10% by weight of the formulation of a low molecular weight silicone wherein the low molecular weight silicone has an average molecular weight of 10,000 or less;
(e) from about 0.1% to about 10% by weight of the formulation of a high molecular weight silicone wherein the high molecular weight silicone has an average molecular weight of 100,000 or greater,
wherein the liquid powder formulation has a percent solids of greater than 30%; and
wherein the liquid powder formulation has an EUI of 300 or greater.

33. The aqueous, non-alcoholic liquid powder formulation of claim 32, further comprising from about 0.1% to about 10% by weight of the formulation of a solid fatty acid ester of a $C_{12}$ to $C_{22}$ fatty acid having a melting point of about 32° C. to about 70° C.

34. The aqueous, non-alcoholic liquid powder formulation of claim 32, wherein the weight percent of the formulation of the water is from about 20% to about 75%.

35. The aqueous, non-alcoholic liquid powder formulation of claim 32, wherein the liquid powder formulation has an OUI of about 0.1 or less.

36. The aqueous, non-alcoholic liquid powder formulation of claim 32, further comprising an additional ingredient selected from the group consisting essentially of fragrances, fragrance solubilizers, colorants, skin health agents, preservatives, and mixtures thereof.

37. The aqueous, non-alcoholic liquid powder formulation of claim 36, wherein the skin health agent is selected from the group consisting essentially of antimicrobial actives, anti-inflammatory agents, antifungal actives, antiviral actives, antiseptic actives, antioxidants, astringents, biological actives, deodorants, emollients, humectants, exfoliants, natural moisturizing agents, skin conditioning agents, skin protectants, antiperspirants, ultraviolet absorbing agents, sunscreens, phytosterols, vitamins, botanicals, and mixtures thereof.

38. The aqueous, non-alcoholic liquid powder formulation of claim 37, wherein the skin health agent is sunscreen.

39. The aqueous, non-alcoholic liquid powder formulation of claim 32, wherein the powder is selected from the group consisting essentially of starches, modified starches, boron nitride, spray dried hydrogenated vegetable oils, oatmeal, titanium dioxide, treated titanium dioxide, zinc oxide, treated zinc oxide, shea butter powder, polyethylene powder, nylon powder, polyamide powder, acylics multipolymer powder, nylon (polyamide) powder, non-swellable natural and/or synthetic clays, organically modified clays, non-solubilized silicone resin powder, non-solubilized PEG-12 dimethicone crosspolymer powder, non-solubilized dimethicone crosspolymer powder, non-solubilized divinyldimethicone/ dimethicone copolymer, microcapsules, and mixtures thereof.

40. The aqueous, non-alcoholic liquid powder formulation of claim 39, wherein the powder is corn starch.

41. The aqueous, non-alcoholic liquid powder formulation of claim 39, wherein the powder is tapioca starch.

42. The aqueous, non-alcoholic liquid powder formulation of claim 39, wherein the powder is oatmeal.

43. The aqueous, non-alcoholic liquid powder formulation of claim 39, wherein the powder is a microcapsule.

44. The aqueous, non-alcoholic liquid powder formulation of claim 43, wherein the microcapsule comprises a shell material selected from the group comprising collagen, gelatin, dextrin, melamine resin, silicone resin, and starch.

45. The aqueous, non-alcoholic liquid powder formulation of claim 43, wherein the microcapsule comprises a core material of a skin health benefit agent.

46. The aqueous, non-alcoholic liquid powder formulation of claim 32, wherein the low molecular weight silicone is selected from the group consisting essentially of dimethicone, amodimethicone, simethicone, hexamethylsiloxane, steroxytrimethylsilane, vinyldimethicone, divinyldimethicone, phenyl propyl trimethicone, diphenylmethicone, phenyl trimethicone, trisiloxane, trimethicone, caprylyl trimethicone, hexymethicone, caprylyl methicone, lauryl methicone, and mixtures thereof.

47. The aqueous, non-alcoholic liquid powder formulation of claim 32, wherein the low molecular weight silicone is dimethicone.

48. The aqueous, non-alcoholic liquid powder formulation of claim 32, wherein the high molecular weight silicone is selected from the group consisting essentially of dimethicone gum, dimethiconol gum, silicone elastomers, acrylates/dimethicone methacrylate copolymers, PEG-12 dimethicone crosspolymer, divinyldimethicone/dimethicone crosspolymer, nylon-611/dimethicone, and mixtures thereof.

49. The aqueous, non-alcoholic liquid powder formulation of claim 48, wherein the high molecular weight silicone is dimethiconol gum.

50. The aqueous, non-alcoholic liquid powder formulation of claim 48, wherein the high molecular weight silicone is dimethicone gum.

51. The aqueous, non-alcoholic liquid powder formulation of claim 32, wherein the polymeric emulsifier is selected from the group consisting essentially of acrylates/alkyl acrylates crosspolymers; acrylates/acrylamide acrylates copolymers, and mixtures thereof.

52. The aqueous, non-alcoholic liquid powder formulation of claim 51, wherein the polymeric emulsifier is acrylates/ $C_{10}$-$C_{30}$ alkyl acrylates crosspolymers.

53. The aqueous, non-alcoholic liquid powder formulation of claim 51, wherein the polymeric emulsifier is acrylates/ acrylamide acrylates copolymer.

54. The aqueous, non-alcoholic liquid powder formulation of claim 32, wherein the weight percent of the formulation of the powder is from about 30% to about 50%.

55. The aqueous, non-alcoholic liquid powder formulation of claim 32, wherein the powder has a mean particle size of about 70 microns or less.

56. The aqueous, non-alcoholic liquid powder formulation of claim 32, further comprising a solid fatty acid ester.

57. The aqueous, non-alcoholic liquid powder formulation of claim 56, wherein the solid fatty acid ester is selected from the group consisting essentially of: myristyl myristate, stearyl benzoate, stearyl behenate, behenyl behenate, cetyl lactate, cetyl esters, stearyl lactate; and, mixtures thereof.

58. The aqueous, non-alcoholic liquid powder formulation of claim 32, further comprising a neutralizing agent.

59. The aqueous, non-alcoholic liquid powder formulation of claim 58, wherein the neutralizing agent is selected from the group consisting essentially of triethanolamine, sodium hydroxide, sodium borate, sodium citrate, and mixtures thereof.

60. The aqueous, non-alcoholic liquid powder formulation of claim 59, wherein the neutralizing agent is triethanolamine.

61. The aqueous, non-alcoholic liquid powder formulation of claim 32, wherein the aqueous, non-alcoholic liquid powder formulation has a pH of about 4 to about 8.

62. The aqueous, non-alcoholic liquid powder formulation of claim 32, wherein the aqueous, non-alcoholic liquid powder formulation has an oil and/or moisture retention value of about 0.5 grams/gram to about 8 grams/gram.

63. The aqueous, non-alcoholic liquid powder formulation of claim 32, wherein the aqueous, non-alcoholic liquid powder formulation is a component of a disposable article or a disposable paper product.

64. The aqueous, non-alcoholic liquid powder formulation of claim 32, wherein the aqueous, non-alcoholic liquid powder formulation is packaged as a lotion to be delivered to the skin in the form from the group comprising squeezable from a container, pumpable from a container, sprayable from a container, spreadable from a roll-on container, dispensable from a container, and dispensable from a container component of a disposable article or paper product.

65. The aqueous, non-alcoholic liquid powder formulation of claim 32, wherein the aqueous, non-alcoholic liquid powder formulation is in the form of an emulsion stick.

66. An aqueous, non-alcoholic liquid powder formulation comprising:

(a) from about 14% to about 75% by weight of the formulation of water;
(b) from about 25% to about 60% by weight of the formulation of a powder;
(c) from about 0.05% to about 1% by weight of the formulation of a polymeric emulsifier;
(d) from about 0.5% to about 15% by weight of the formulation of a low molecular weight silicone wherein the low molecular weight silicone has an average molecular weight of 10,000 or less;
(e) from about 0.1% to about 10% by weight of the formulation of a high molecular weight silicone wherein the high molecular weight silicone has an average molecular weight of 100,000 or greater,
wherein the liquid powder formulation has a percent solids of greater than 30%; and
wherein the liquid powder formulation has an OUI of 0.1 or less and an EUI of 300 or greater.

67. The aqueous, non-alcoholic liquid powder formulation of claim 66, further comprising from about 0.1% to about 10% by weight of the formulation of a solid fatty acid ester of a $C_{12}$ to $C_{22}$ fatty acid having a melting point of about 32° C. to about 70° C.

68. The aqueous, non-alcoholic liquid powder formulation of claim 66, wherein the weight percent of the formulation of the water is from about 20% to about 75%.

* * * * *